United States Patent [19]
Bosredon

[11] Patent Number: 6,117,175
[45] Date of Patent: Sep. 12, 2000

[54] SPHERICAL KNEE JOINT PROSTHESIS

[76] Inventor: Jean Bosredon, 78 avenue de la République, 33200 Bordeaux, France

[21] Appl. No.: 08/920,927

[22] Filed: Aug. 29, 1997

Related U.S. Application Data

[63] Continuation-in-part of application No. 08/293,898, Aug. 22, 1994, abandoned.

[51] Int. Cl.[7] ........................................... A61F 2/38
[52] U.S. Cl. ..................... 623/20.15; 623/20.22; 623/20.32; 623/20.33
[58] Field of Search ................... 623/20, 18, 16, 623/20.14, 20.15, 20.21–20.23, 20.27–20.36

[56] References Cited

U.S. PATENT DOCUMENTS

| | | |
|---|---|---|
| 3,694,821 | 10/1972 | Moritz . |
| 3,795,922 | 3/1974 | Herbert et al. ............................. 623/20 |
| 3,868,730 | 3/1975 | Kaufer et al. .............................. 623/20 |
| 3,869,729 | 3/1975 | Attenborough . |
| 4,085,466 | 4/1978 | Goodfellow et al. . |
| 4,094,017 | 6/1978 | Matthews et al. . |
| 4,205,400 | 6/1980 | Shen et al. . |
| 4,224,697 | 9/1980 | Murray et al. ............................. 623/20 |
| 4,249,270 | 2/1981 | Bahler et al. . |
| 4,268,920 | 5/1981 | Engelbrecht et al. ...................... 623/20 |
| 4,538,306 | 9/1985 | Dorre et al. ............................... 623/20 |
| 4,662,889 | 5/1987 | Zichner et al. . |
| 5,597,384 | 1/1997 | Walker et al. ............................. 623/18 |
| 5,776,201 | 7/1998 | Colleran et al. ........................... 623/20 |
| 5,782,923 | 7/1998 | Engelbrecht et al. ..................... 623/20 |
| 5,782,925 | 7/1998 | Collazo et al. ............................ 623/20 |
| 5,800,552 | 9/1998 | Forte ......................................... 623/20 |
| 6,039,764 | 3/2000 | Pottenenger et al. ................. 623/20.21 |

FOREIGN PATENT DOCUMENTS

| | | |
|---|---|---|
| 0126978 | 12/1984 | European Pat. Off. . |
| 4102509 | 7/1992 | Germany . |
| 2088724 | 6/1982 | United Kingdom . |

*Primary Examiner*—David H. Willse
*Assistant Examiner*—Suzette J. Jackson
*Attorney, Agent, or Firm*—Plunkett & Cooney, P.C.

[57] ABSTRACT

A replacement prosthesis for replacing an earlier implanted prosthesis comprises a femoral implant and a tibial implant cooperatively configured to enable first and second degrees of articulation. The femoral implant comprises a bicondylian part comprising a pair of condyles disposed so as to form an intercondylian notch and a posteriorly extending hemispherical cavity of the pair of condyles. The tibial implant comprises a tibial base, a catch mounted to the tibial base, and at least one disc removably mounted to the tibial base. The condyles are rotatably slidable on the disc to provide the first articulation. The catch member comprises an end portion which is provided with a spherical head accommodated within the central cavity of the condyles so as to provide the second articulation. The spherical head and the disc are selected from a set of heads and discs having appropriate heights and thicknesses such that a proper ligamentary tension can be obtained.

22 Claims, 7 Drawing Sheets

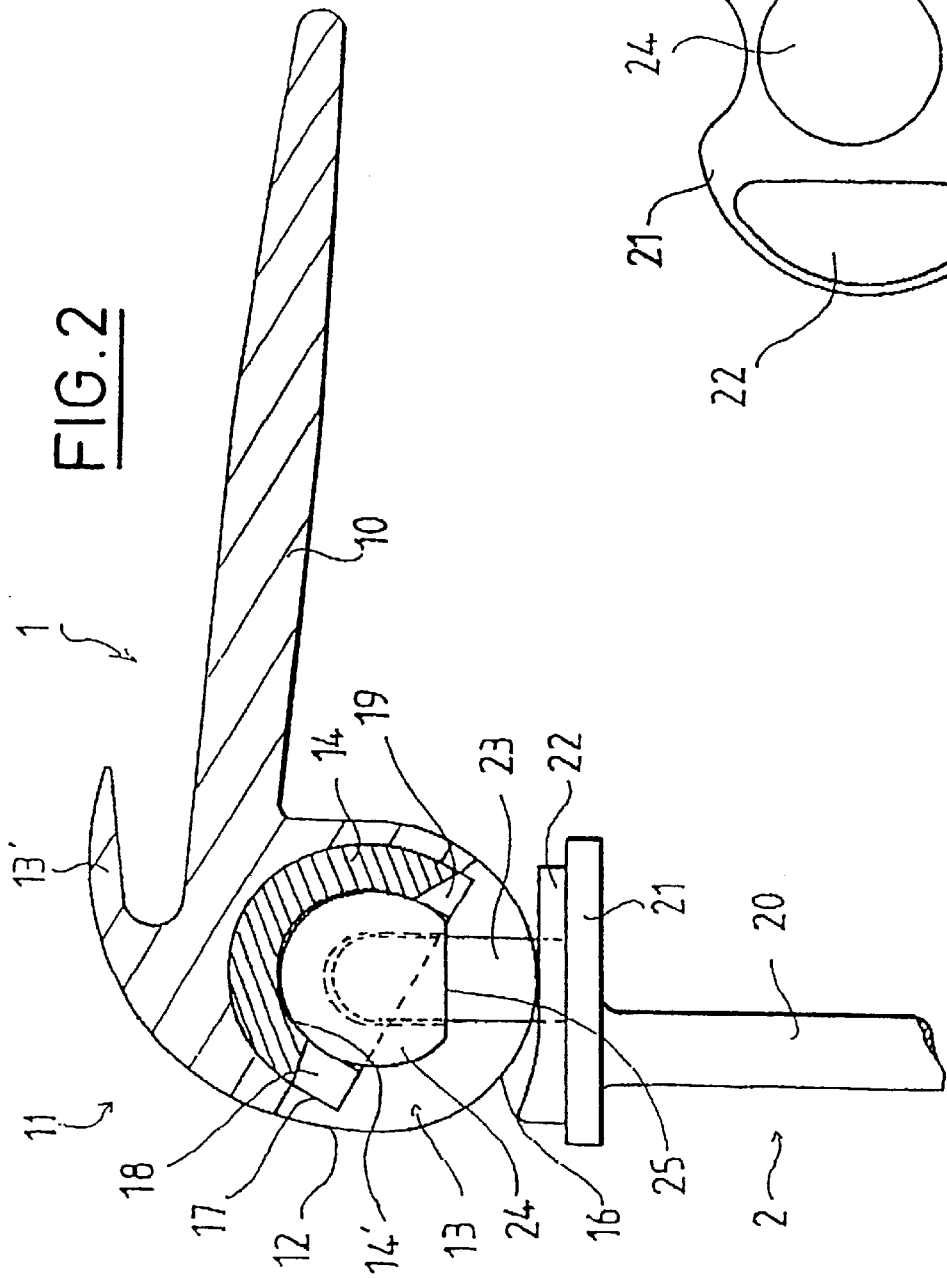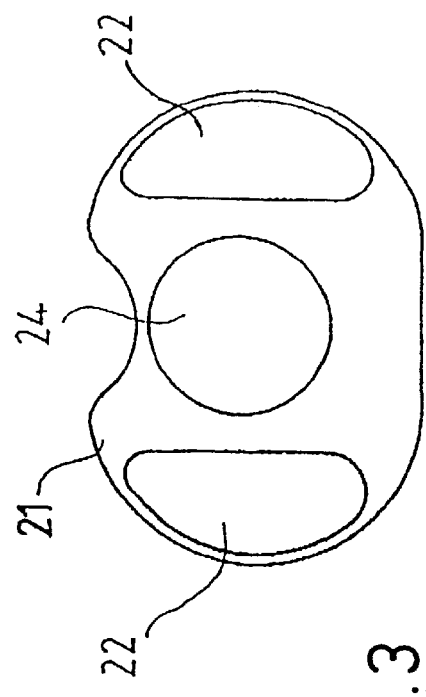

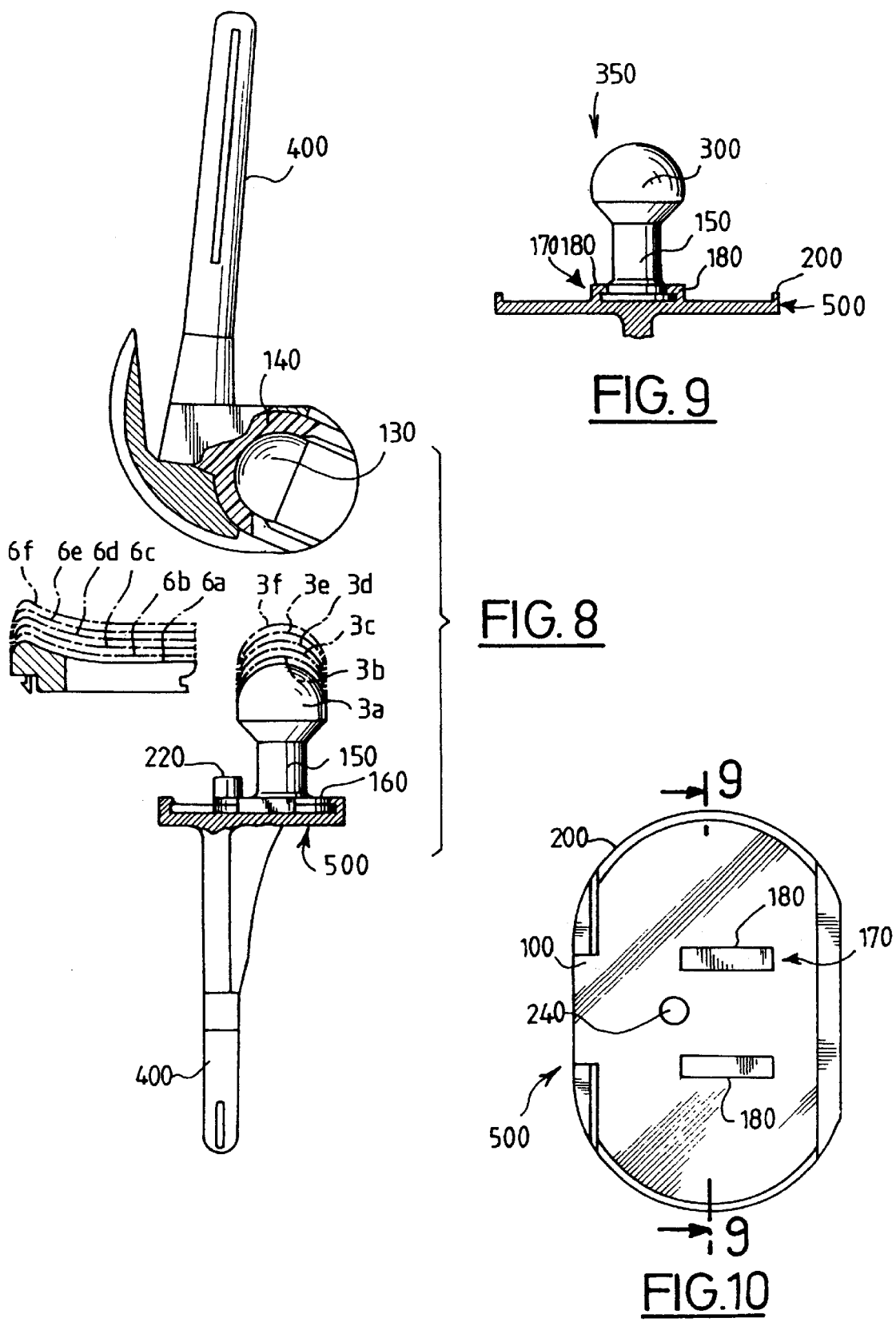

SPHERICAL KNEE JOINT PROSTHESIS

CROSS-REFERENCE TO RELATED APPLICATION

This application is a continuation-in part application of application Ser. No. 08/293,898, filed Aug. 22, 1994 now abandoned for "Synthetic Knee Prosthesisr", the disclosure of which is incorporated by reference.

BACKGROUND OF THE INVENTION

1. Field of the invention

The subject matter of the present invention is a replant knee joint prosthesis assembly replacing a previously implanted prosthesis.

2. Prior Art

The replacement prosthesis must satisfy increased constraints, since the knee of the patient no longer has ligaments.

A replacement prosthesis must, despite the absence of ligaments, and most of the time due to the advanced age of the patient, substantially permit the latter to ensure a safe working of the articulation system, whatever the complexity of the movement of this articulation.

In fact it is a compromise between the muscular means of the patient that are at the disposal of the surgeon and the higher possibility of movement that a safe technology can offer.

In this manner appeared the replacement prostheses which are still little used at the present time, but which tend to be more and more used due to the quick increase of the lifetime of patients.

A knee joint prosthesis has to attempt to reproduce the different rotations of the natural articulation. However, a replacement prosthesis cannot perform these to the same extent and the constraints that are attributed to it are somewhat less important.

Generally speaking, it can be said that a good replacement prosthesis should satisfy qualities well higher than the hinged articulated prosthesis, i.e. a prosthesis the articulation of which is mechanically constrained by a connection axis and so can move only in one plane, the sagittal plane. Additionally, this good replacement prosthesis must allow the closest possible movement from the prosthesis, the so called posterostabilized movements, that tend to reproduce the natural knee articulation, without however allowing the smallest dislocation or release of the mechanical members between them.

The knee prosthesis with a patella joint articulation satisfies the criteria of a replacement prosthesis; this comes From the fact that the patella is a sphere which is necessarily located at the center of rotation and is used as a central support of the articulation, without for this reason constraining the latter during its movements. This is true if the latter brings both condyles to a friction identical or quasi identical on corresponding portions of the tibial disc or plate, or if one of the condyles is more strongly than the other put into contact with its corresponding portion of the tibial disc.

However, this kind of articulation does not exclude to respect the articulation interline of both knees of the patient, which, to allow the patient a good reproduction of working, requires that the articulations of each knee, and consequently their respective contact lines, lie in the same horizomtal plane, It must then be possible to technically act to this end.

Today, a few patents disclose a knee joint prosthesis with a patella articulation.

For example, U.S. Pat. No. 3,868,730 teaches a prosthesis of which the tibial shank, the tibial base plate slidingly receiving the condyles, and the articulation sphere, are made in one piece, thus making impossible any adjustment of the articulation interline and increasing subsequent wear and tear on the tibial disc, Moreover, the presence of the patella or sphere, in extension from the tibial shank, constitutes, in the working space between the femoral distal area and the tibial proximal area, a trouble for the working of the surgeon during the mounting of the femoral element.

Also the German patent DE 4 102 509 discloses a prosthesis with a patella joint articulation in which the catch and head assembly, which is removable, is introduced into an accommodation bore performed on the tibial system and has a length sufficient for efficiently resisting the miscellaneous mechanical constraints exerted on the patella joint head Due to the offset between the catch axis and the axis of the tibial system, the latter must be very cumbersome. This requires an intramedullar canal of corresponding size, and therefore entails a partial destruction of the bone capital, which considerably renders the canal brittle.

In this prosthesis, as in the British Patent GB-A-2 088 724, the joint is essentially realized between the condyles and the tibial discs. However, there is still wear and tear on the tibial disc.

At last, the European Patent EP-A-0 639 358 also discloses a ball and socket knee joint prosthesis in which the element forming the catch is in one piece with the tibial shank and the disc supporting plate. This assembly is integral as is the assembly of U.S. Pat. No. 3,868,730, but the ball head, instead of being part of this block, is interchangeable. As in the above U.S. patent, the catch of the prosthesis disclosed by this European patent must necessarily be attached to the stem and plate member (tibial base), as all mechanical efforts developed on the articulation are added to the same amplified efforts of the spherical head, itself mounted on the head portion of the catch. If the bearing surface of the head on the catch is small, this arrangement is not satisfying.

In this European patent, for adjusting the location of the articular interline in the horizontal plane formed with the plane of the other knee, it is sufficient to have tibial plates of different thicknesses and ball heads whose machining of the fitting diameter on the catch end is sufficiently reduced for allowing a total or partial fitting, the effect of which is to slightly raise the articulation.

Finally, the solutions proposed according to the prior art are poorly adapted, expensive and have a low safety. Indeed, it is never possible to modify the catch height since the latter is stationary and attached to the prosthesis which, as has become a rule for orthopedic surgeons, must respect as well as possible the bone capital of the patient.

The present invention specifically concerns a ball and socket joint replacement prosthesis, in which the catch supporting the spherical head is always offset from the stem or shank axis, which corresponds to the axis of the tibial intramedullar canal.

Sliding prostheses, which are so far the most comfortable, comprise a tibial implant which rolls and slides on the femoral implant. These prostheses are very close to a natural joint.

Sliding prostheses present nevertheless a disadvantage, i.e., a possible displacement translating itself by an anterior sliding and particularly a lateral one. This inconvenience appears notably when a replacement prosthesis is implanted when replacing a previous prosthesis.

On the other hand, sliding prostheses exhibit a dilapidation of the tibial part due to the wear and tear on the disc, which generally is formed from polyethylene, by chafing on the femoral implant.

The major inconvenience of these prostheses comes from the loss of freedom of movement of one piece with respect to the other, limiting the joint to function only in one plane, the sagittal plane To address these problems there has been developed a sliding knee prosthesis equipped with a centering stud which avoids the sliding phenomena, for example the prosthesis described in above commented GB-A-2 088 724 and DE-A-4 102 509.

The present invention aims to remedy these diverse disadvantages while proposing a highly durable spherical knee joint prosthesis, prohibiting all transitory movement of one piece with respect to the other while allowing their rotation.

SUMMARY OF THE INVENTION

The knee prosthesis according to the present invention comprises a tibial implant and a femoral implant characterized by (a) a femoral implant comprising a bicondylian part comprising a pair of condyles disposed so as to define an intercondylian notch and a posteriorly extending hemispherical cavity central of the pair of condyles, (b) a tibial implant comprising a tibial base, a tibial rod forming an intramedullary shank, at least one disc removably mounted to said tibial base, on which said pair of condyles is rotatably slidable, and which provides a first articulation, a catch mounted to the base, the catch comprising an end portion and which is provided with a spherical head accommodated within said central cavity of said pair of condyles so as to provide a second, spherical articulation between said femoral implant and said tibial implant, and (c) said spherical head and said at least one disc being selected from a set of heads and discs having appropriate heights and thicknesses such that a proper ligamentary tension ran be obtained for a patient.

According to an embodiment of the invention, said spherical head is formed by a cupule disposed in the central cavity and the cupule has a hemispherical cavity provided therein for accommodating the end portion of the catch, means for removably mounting the at least one disc to the tibial base are provided, and the spherical cupule can slidably seat in the hemispherical cavity of said condyles such that there is substantially not any lateral play between each of the pair of condyles and the at least one disc.

The tibial disc of the prosthesis according to the invention can be joined at is base in a detachable manner by any appropriate means, for example by clipping. It can also be simply positioned on the tibial base in a manner allowing it to displace itself at the time of knee movement, its mobility being in this case limited by any known device, for example the interdependent pins of the base.

The tibial base of the prosthesis according to the invention can be fixed to the bone as by any appropriate known means, for example with the aid of a screw or by embedding as well as by an intramedullary anchoring shank.

The length of the intramedullary femoral shank and, if necessary, the intramedullary tibial shank can be variable. The length can be modified by fixing the segments of the shank with the help of known mechanical means.

After implanting the femoral and tibial implants, they are assembled one to the other by the introduction of the spherical head of the tibial implant in the hemispherical cupule of the femoral implant, the latter comprising a trochlean part which extends the condyles and is susceptible of articulating itself with a patellar implant of any known type.

To mitigate the disadvantages of laxity related to the problems of the bone tissue cut and ligamentary tension, the depth of the spherical head can be varied to a disc thickness corresponding to each head depth. Depending on the chosen head depth, the femur or the tibia can be moved to stretch the lateral ligaments until they are not injured and thereby achieve ligamentary balance.

The hemispherical cupule of the femoral implant can be either simply hemispherical, or hemispherical with sides extending beyond the diameter so as to prevent dislocations, or may be a retention hemispherical configured in such a way as to retain the spherical head. The recovery of the spherical head must be sufficient to prevent all anterior or posterior dislocations of one piece with respect to the other. In this manner the play economized between the bicondylian surface of the femoral implant and the discs or the semi-discs of the tibial implant, ensure no mechanical function other than that of limiting the movement in a frontal plane (varus-valgus).

With time the wear and tear of the cupule, by the rubbing of the spherical head, brings together the femoral and tibial pieces one to the other, and play is reduced. When this play has disappeared, the femoral condyles come into contact with the tibial disc. At this moment, the rubbing together is no more than that of the head an the cupule and the condyles an the tibial disc. This play permits the augmentation of the longevity of the prosthesis and allows the patient to avoid a new surgical intervention to change the worn pieces.

Anterior slide and lateral laxity being impossible and the varus-valgus movements being limited, all other rotations under constraints, or without constraints, are permitted by the prosthesis according to the present invention.

According to another possible embodiment of the knee joint prosthesis assembly, the cupule has a conical cavity formed therein for accommodating the end portion of the catch, and said cupule is selected from a set of cupules whose cavities have different opening angles, for example conical angles, in order to permit an adjustment of the height of said spherical articulation for obtaining a proper ligamentary tension.

The advantages and the characteristics of the preset invention will become more clearly evident by the description which follows and which relate to the annexed drawings.

In the annexed drawings:

BRIEF DESCRIPTION OF THE DRAWINGS

FIG. 2 represents a partial side view of the prosthesis of FIG. 1, with a cut according to a median plane of the femoral implant;

FIG. 3 represents a plane view of the tibial implant of the prosthesis of FIG. 1;

FIG. 8 is a side view and partial cut of a set of knee joint prostheses according to the embodiment of FIG. 7 including one-piece members, heads-catches of different heights, and an assembly of tibial discs of corresponding thicknesses;

FIG. 9 is a sectional view taken along line 9/9 of FIG. 10 showing the one-piece spherical head-catch member and its base plate introduced in the sliding member of the tibial base;

FIG. 10 is a plane view of the tibial base of the prosthesis of FIG. 7;

DETAILED DESCRIPTION OF THE PREFERRED EMBODIMENTS

Figure 1:
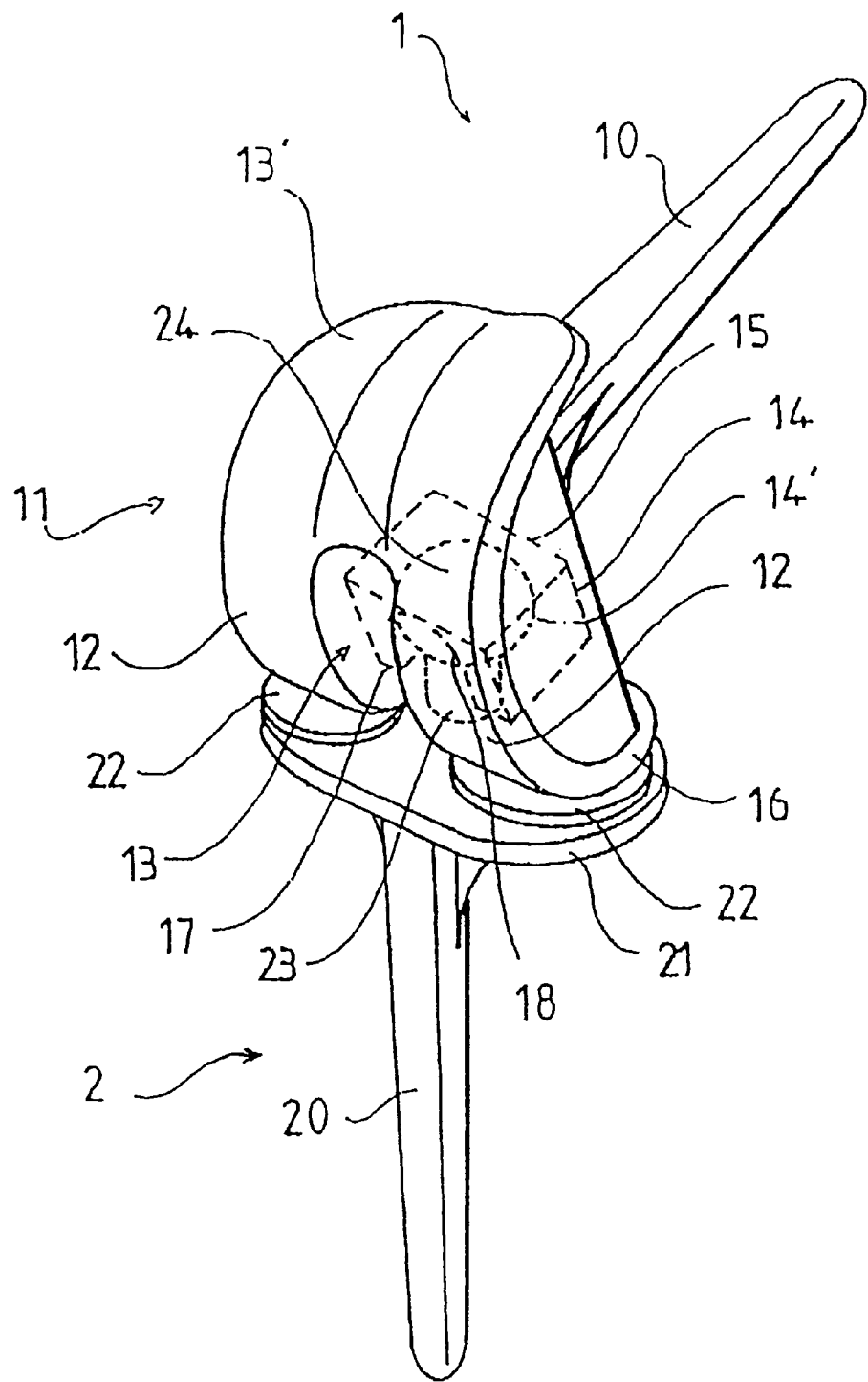
FIG. 1 represents a perspective view of a first embodiment of a knee joint prosthesis of the assembly according to the present invention, in a semi-flexed position.

Referring to FIGS. 1 and 2, there is shown a first embodiment of a knee prosthesis according to the present invention which comprises a femoral implant 1 and a tibial implant 2.

The femoral implant 1 comprises an intramedullary shank 10 which terminates in a distal zone by a bicondylian part 11. The bicondylian part 11 comprises two condyles 12, two posterior condyles 16, and an intercondylian notch 13.

The femoral implant 1 may comprise an anatomical trochlesa 13', in which case the patella articulates itself with the anatomical femoral trochlea 13'.

The bicondylian part 11 has a cavity 15 positioned with regard to the intercondylian notch 13 and-oriented toward the posterior condyles 16, and in which is disposed a cupule 14 presenting a hemispherical cavity 14'.

Figure 4:
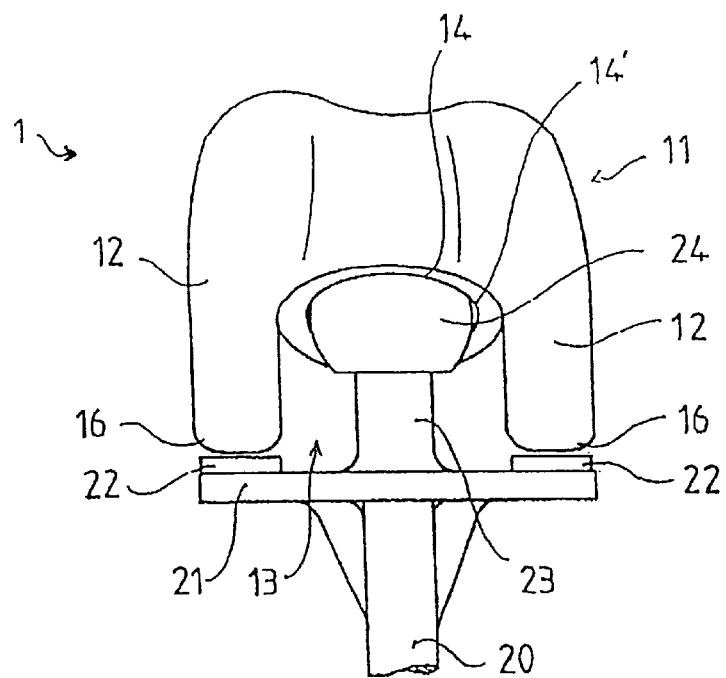
FIG. 4 represents a partial side view of the prosthesis of FIG. 1 in the semi-flexed position.

Referring to FIGS. 2 through 4, there is depicted the tibial implant 2 which comprises an intramedullary shank 20 surmounted on a tibial base 21 on which are joined two removable semi-discs 22. The discs 22 are removably mounted to the tibial base 21 by any known means.

The tibial base 21 further comprises a tronconic catch 23 disposed centrally and posteriorly between the semi-discs 22 (not visible in FIG. 3). At the extremity of the catch is fixed a spherical head 24 having a tronconic orifice 25. The spherical head 24 has a diameter equal to that of the hemispherical cavity 14' of the cupule 14, this diameter being variable from 10 to 40 mm.

After implantation of the tibial implant 2, the fernoral implant 1 and the tibial implant 2 are assembled by insertion of the spherical head 24 in the hemispherical cavity 14' of the cupule 14.

At the time of the surgical operation (usually a replacement operation), a plurality of spherical heads 24, where the orifices 25 are of different conicities, are at the disposition of the surgeon in a manner such that the one best adapted for ligamentary tension can be chosen. The surgeon likewise arranges the semi-discs 22 of different depths permitting, after selection of the spherical head 24, to choose the semi-discs 22 of the depth which is best adapted to allow to subsist a minimum play between the condyles 12 and the semi-discs 22.

As shown in FIGS. 1 and 2, the cupule 14 comprises a side 17 stretching the cupule to the diameter of the hemispherical cavity 14'. The side 17 is hollowed in two grooves 18 and 19 whose width permits the passage of the catch 23, diametrically opposed, with regard to the intercondylian notch 13, in such a manner so as to not limit the flexing and extending movements.

Such a prosthesis enables the constraints to be uniquely applied to the cupule formed by the spherical head 24 and the hemispherical cavity 14', prohibiting any lateral play. Contrariwise the movements in the frontal plane are limited to the play existing between the condyles 12 and the tibial discs 22, as seen in FIG. 4.

All of the rotations in the sagittal plane are such that the internal or external rotations of the tibia with respect to the femur are permitted, with or without constraints.

Figures 5, 6:
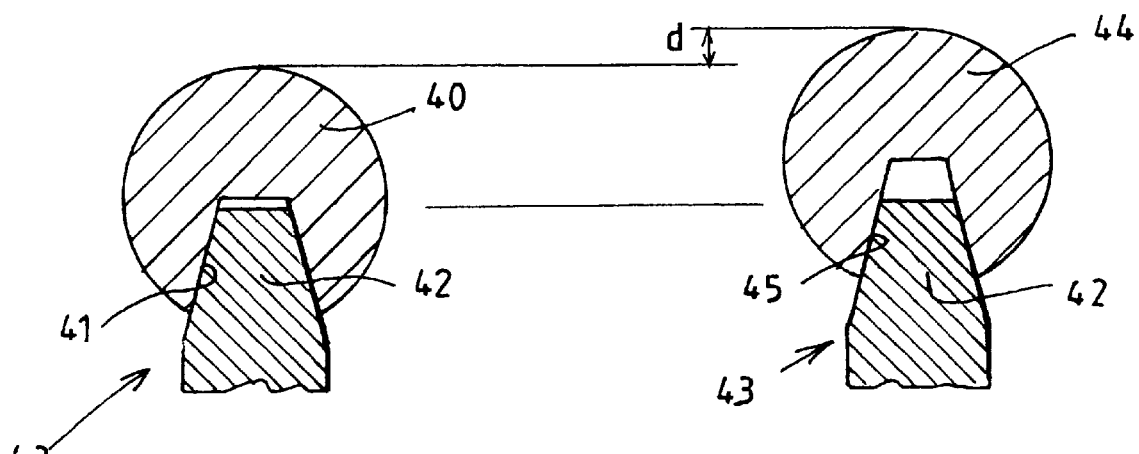
FIG. 5 represents a partial side view and partial cut of a second embodiment of the knee joint prosthesis of the assembly according to the present invention.
FIG. 6 is a view similar to FIG. 5 showing the same embodiment as FIG. 5 but with a different shape of the cavity inside the cupule.

FIGS. 5 and 6 show an embodiment of the knee joint prosthesis of the present invention in which the spherical head 40 has a cavity 41 formed therein for accommodating the end portion 42 of the catch 43, this end portion having a correspondingly conical surface. The cavity 41 opens outside and has a suitable shape, for example conical. The head 40 is selected from a set of heads whose cavities 41 have different opening angles in order to permit an adjustment of the height of the spherical articulation 40, 41 for obtaining a proper ligamentary tension.

FIG. 6 shows a second spherical head 44 whose internal conical cavity 45 is narrower, i.e. has a lower opening angle, whilst the internal wall keeps the same slope. Since the conical top portion 42 of catch 43 is standard, the spherical head 44 of FIG. 6 is consequently positioned higher than the spherical head 41, from a distance d. In all other respects, the embodiment of FIGS. 5–6 is the same as the embodiment of FIGS. 1–4.

FIGS. 7–11 show a third embodiment of the replacement knee prosthesis of the present invention.

This knee prosthesis is specially adapted to constitute a replacement prosthesis like the embodiment of FIGS. 1–4. It includes a tibial implant 100 and a femoral implant 200 articulated on each other by means of a member 3 comprising a spherical articulation head 300, a catch 150, and a base plate 160, as described further hereinbelow.

The tibial implant 100 comprises a tibial stem or shank 400 shaped in order to be able to be introduced into the intramedullar canal of the patient's tibia, a tibial base 500 attached to the shank 400 and adapted to receive a tibial plate 600. The femoral implant 200 includes a stem 70 attached to condyles 80, 90 suitably shaped, in order to be able to slide and be articulated on conjugated surfaces 110, 120 of the tibial plate 600. The latter is formed in a suitable plastic material, whilst other 1elements of the prosthesis are metallic.

The ball joint or spherical head 300 can be accommodated within a corresponding cavity 130 of a socket or cupule 140 in plastic material, mounted within implant 200 between condyles 80 and 90. The femoral implant 200 is designed in a manner known per se, and does not require element supplemental disclosure.

The ball joint or head 300 is formed in one piece with a catch 150, which itself is made in one piece with a base plate 160 that can be attached on the tibial base 500 in a removable manner.

The base plate 160 can slide within a slide member 170 formed by a pair of parallel ramps 180 having an inverted L cross-section. These ramps 180 extend in antero-posterior planes and are separated by a gap substantially corresponding to the width L of a recess 190 formed in the central area of the tibial plate 600 for allowing the passage of the catch 150. As noted, the ramps 180 define a recess 190 for passage of the base plate 160, and are disposed within an area defined by a perimetral edge 171 extending from the periphery of the tibial base 500.

Figure 7:
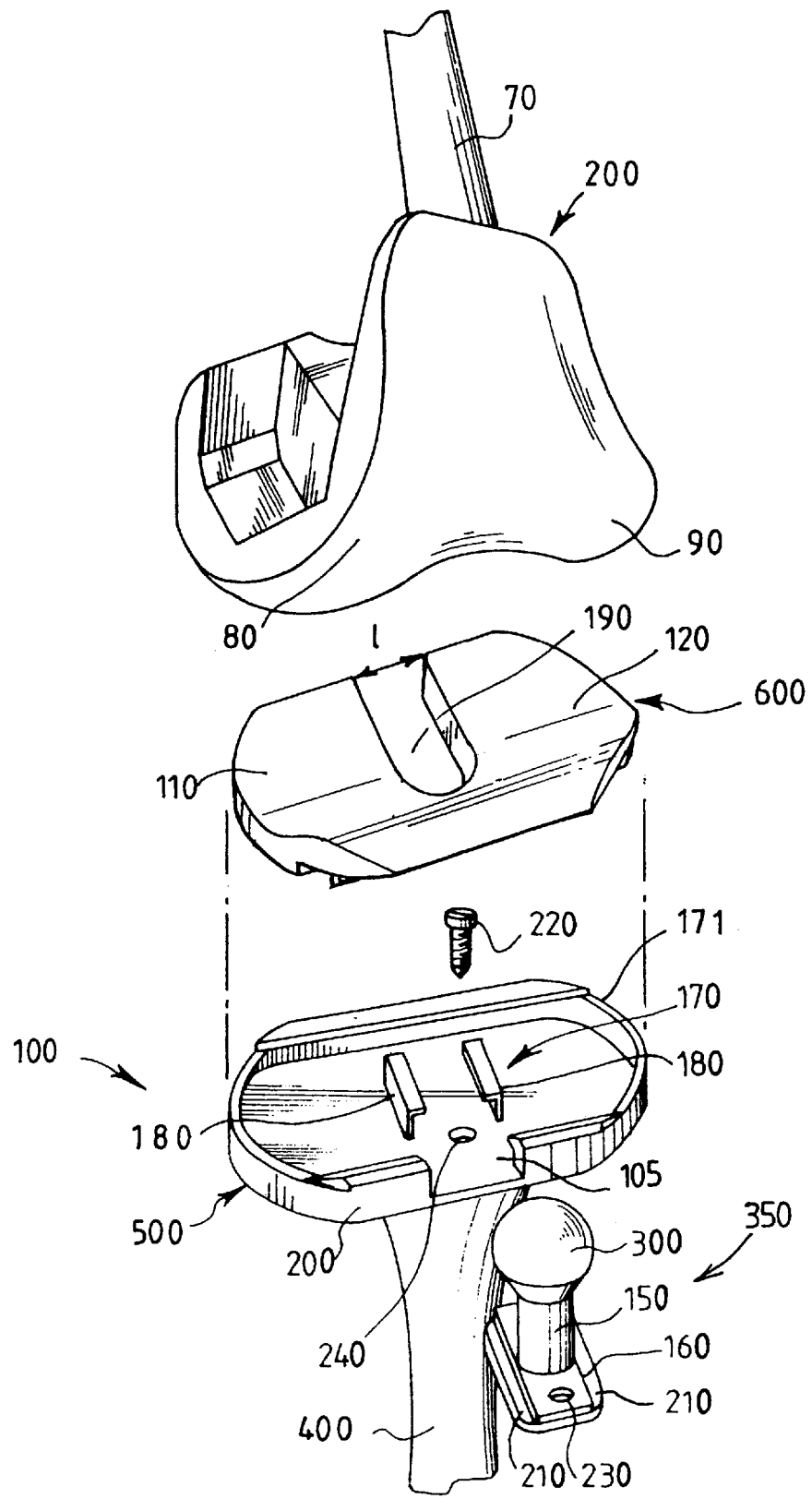
FIG. 7 is an exploded perspective view, in a reduce scale, of a third embodiment of the knee joint prosthesis according to the present invention.

In order to be suitably adapted to the ramps 180, the base plate 160 has a pair of longitudinal edges shaped correspondingly, i.e. each having a step 210 which is adapted to the inverted L shape of the ramp 180. After the one-piece assembly constituted by the ball joint 300, its catch 150, and the base plate 160 has been positioned within the slide member 170, this assembly can be secured by any appropriate means for securing. The means for securing in FIG. 7 is a screw 220, a threaded hole 230 formed in the interior portion of the base plate 160, the screw 220 being screwed in a second threaded hole 240 of the tibial base 500.

Figure 11:
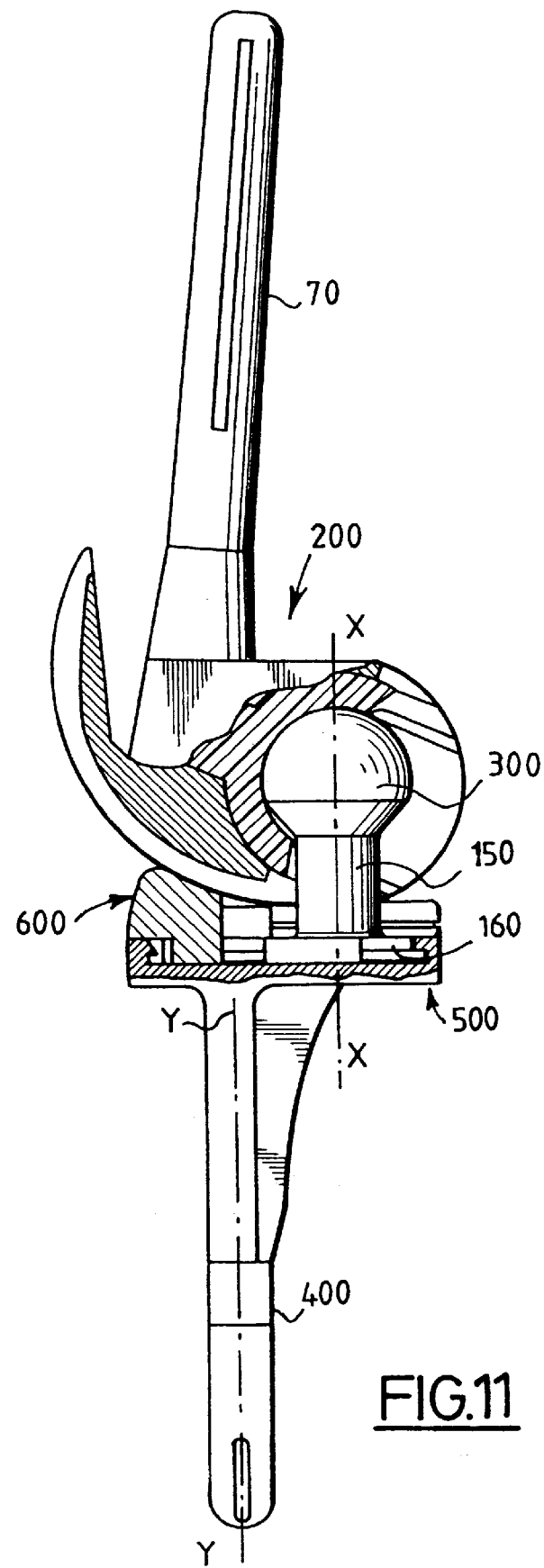
FIG. 11 is a side view with partial cut of the knee joint prosthesis of FIG. 7 in the assembled state, with its femoral implant articulated on the spherical head of the tibial implant.

As seen in FIG. 11, the axis X of the catch 150 and of the ball joint or head 300 is offset in the rearward direction from axis Y of the tibial stem 400.

The screw 220 is positioned forward from the catch 150, in order to be substantially located in the axis Y of the stem 400, within which it therefore can be screwed through the tibial base 500.

As noted, the member 3 comprises the head 300, the catch 150, and the base plate 160. The present invention contemplates the member 3 being formed in a plurality of heights, such as are shown in FIG. 8 as 3a-3b-3c-3d-3e-3f. The present invention further contemplates the tibial plate 600 being formed in a plurality of heights corresponding to the plurality of heights of the member 3. The plurality of heights of the member 3 increase according to a suitable arithmetic progression, for example 2 mm. This increase of height comes from an increase of the head height, the catch 150 and the base plate 160 keeping the same height from one piece to the other.

Correlatively, the tibial plates 600 must have thicknesses increasing in the same ratio or proportion from a first plate 6a having a minimum thickness, until the last plate 6f having a maximum thickness, corresponding to head 3f. The thicknesses of these plates increase by the same value from each plate to the next as do heads 3a, 3b, . . . , in order to compensate for the play which otherwise would appear between the surface of the condyles 80, 90 and the sliding surfaces 110, 120 of the tibial plates 600 (FIG. 11).

The progression of the heights of the members 3 and of the thickness of the tibial plates 600 is advantageously an arithmetical progression, for example with a step of 2 mm, permitting an increase of 10 mm in the height of the member 3 from the lowest height 3a to the highest height 3f, and in a similar manner the thickness of the thinnest plate 6a to the thickness of the thickest plate 6f.

The total height of the member 3 can be, for example, 10 to 20 mm.

The number of members 3 and corresponding tibial plates 600 can vary, and similarly the amplitude of their height and thickness progression. according to the specific needs of patients.

The member 3 is formed from a material satisfying for its compatibility with the articulation cupule 140, which is, preferably, formed from polyethylene as concerns friction. Stainless steel is a preferred material for the member 3 in its different sizes, as it is both inexpensive and compatible with an articulation cupule 140 made from polyethylene, Due to the fixation of the head 300 on the catch 150, any mechanical stress of heads on catches is avoided.

Additionally me fact that the catch 150 is removable with the head 300 from the tibial base 500 avoids disturbing the surgeon during the surgical intervention by the presence 300 from the tibial base 500 of a stationary catch, avoiding a problem of U.S. Pat. No. 3,868,730.

Besides, due to the manufacturing of sets of members 3 of different heights and of tibial plates 600 having corresponding thicknesses, the surgeon can quite satisfactorily adept this prosthesis to each patient, without being for this reason obliged each time to change the support tibial shank, as it is the case when the tibial shank forms a one-piece member with the catch and the head.

The L-shaped ramps 180 can be charmed to any other suitable system, for example dovetail shapes, which also ensure a good repartition on the tibial base 500 of the efforts exerted by the head 300.

Figure 12:
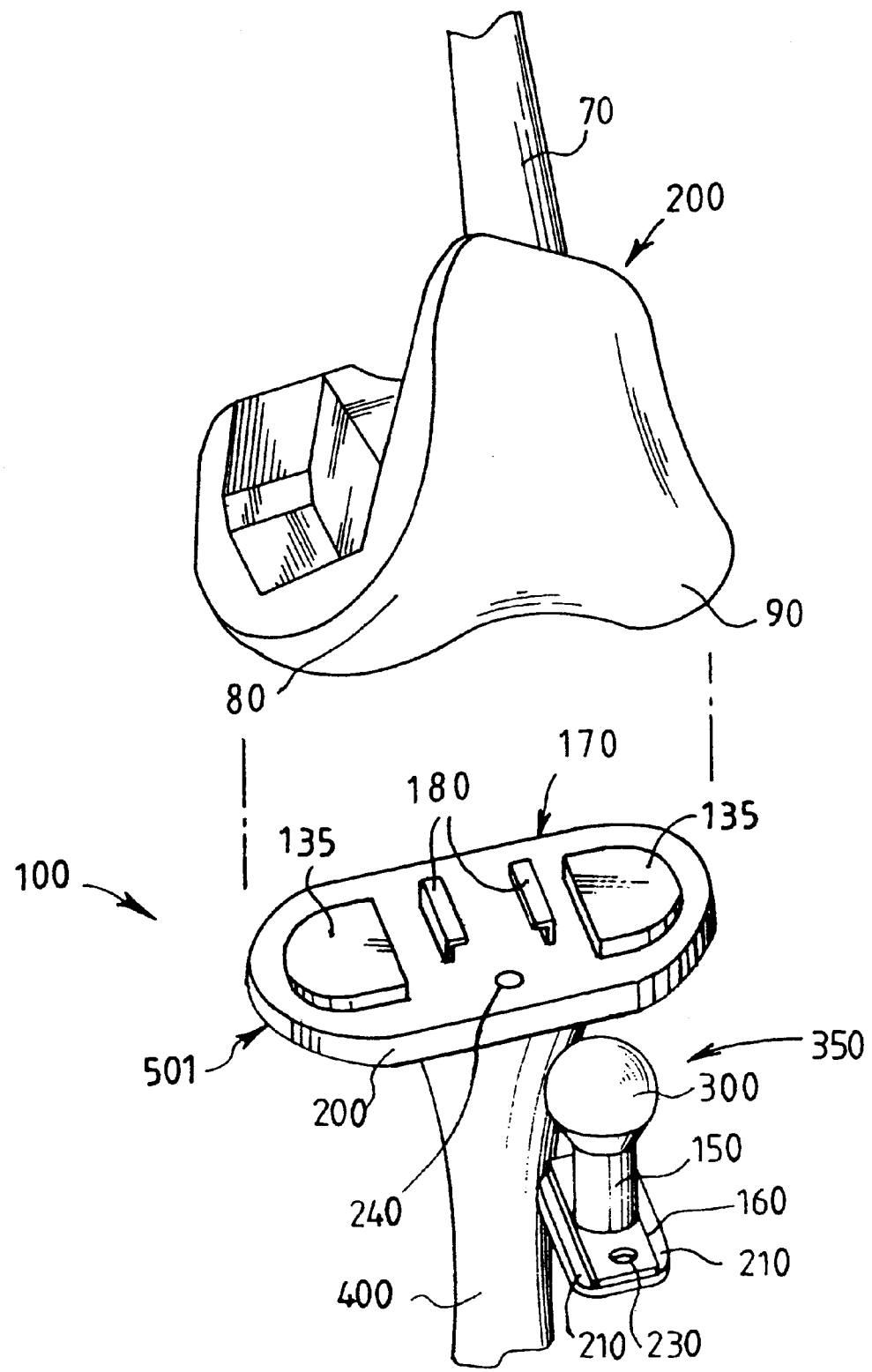
FIG. 12 is an exploded perspective view of a further embodiment of the knee joint prosthesis according to the present invention.

FIG. 12 shows a fourth embodiment of the present invention, similar to the embodiment of FIGS. 7–11. In the embodiment of FIG. 12, the tibial plate 600 has been canceled and changed to two semi-discs 135, each lying on one side of the parallel ramps 180. Additionally the edge 171 (FIG. 7) extending from the surface of the tibial base 500 and retaining the tibial plate 600 has been removed so that the semi-discs 135 can freely rotate and be translated on the surface of the tibial base 501.

Thus, like the preceding embodiments, the knee prosthesis assembly of FIG. 12 ensures a double articulation: a first articulation provided by the condyles 80, 90 rotatably slidable on the discs or semi-discs 135 lying on the tibial base 501, and a second articulation provided between the spherical head 300, accommodated within the central cavity of the pair of condyles between the femoral and tibial implants.

The discs 135 and the spherical head 300 can be selected in a set of heads and discs having appropriate heights and thicknesses, such that a proper ligamentary tension can be obtained for the patient as in the embodiment of FIGS. 7–11.

In the embodiment of FIG. 12, the freedom of movement is increased by the fact that the discs 135 can freely rotate and effect translations on the tibial base 501, which was not the case in the embodiment of FIGS. 7–11.

Due to the fact that the head 300, catch 150 and base plate 160 are made in one piece, the spherical head 300 remains stationary with respect to the catch 150 without mechanically stressing the same. Besides, the connection through a slide member formed on the tibial base supporting the tibial plate (600 or 135) allows a better repartition of the efforts on the base plate 160.

As previously pointed out, not only the work of the surgeon is made easier by the present invention, but besides he is not disturbed in its working space by the presence of an extending element formed by the catch, and he can very specifically adapt the prosthesis elements in relationship to the particular needs of the patient.

The embodiment of FIGS. 7–11 can be modified by removing the peripheral edge 171 retaining the tibial plate 600. Thus the tibial plate 600 becomes freely movable in rotation and translation and provides a second articulation in rotation, as in the other embodiments of the invention.

In all other respects, the embodiment of FIG. 12 is the same as the embodiment of FIGS. 7–11.

While the invention has been illustrated and described in detail in the drawings and the foregoing description, the same is to be considered as illustrative and not restrictive in character, it being understood that only the preferred embodiment has been shown and described fully and that all changes and modifications that come within the spirit of the invention are desired to be protected.

Having, thus, described the invention, what is claimed is:

1. A replacement knee prosthesis assembly for replacing an earlier implanted prosthesis, the replacement prosthesis comprising:

(a) a femoral implant comprising a bicondylian part comprising a pair of condyles disposed so as to define an intercondylian notch and a posteriorly extending hemispherical cavity central of the pair of condyles, (b) a tibial implant comprising a tibial base, at least one disc removably mounted to said tibial base, on which said pair of condyles is rotatably slidable, and which provides a first articulation, a catch mounted to said tibial base, the catch comprising an end portion, and which is provided with a spherical head accommodated within said central cavity of said pair of condyles so as to provide a second spherical articulation between said femoral implant and said tibial implant, and (c) said spherical head and said at least one disc being configured to be selectively attached with the assembly, and being selected from a set of heads and discs having appropriate height and thicknesses such that a proper ligamentary tension can be obtained for a patient.

2. The replacement knee prosthesis assembly of claim 1, wherein said spherical head is formed by a cupule disposed in the central cavity and the cupule has a hemispherical cavity provided therein for accommodating the end portion of the catch, means for removably mounting the at least one disc to the tibial base are provided, and the cupule can slidably seat in the hemispherical cavity of said condyles such that there is substantially not any lateral play between each of the pair of condyles and the at least one disc.

3. The replacement knee prosthesis assembly of claim 2, wherein the at least one disc removably mounted to the tibial base is formed of a plastic material.

4. The replacement knee prosthesis assembly of claim 3, wherein the plastic material is polyethylene.

5. The replacement knee prosthesis assembly of claim 2, wherein the spherical head of the tibial implant has a diameter equal to the diameter of the hemispherical cavity of the cupule disposed in the cavity defined by the pair of condyles of the femoral implant.

6. The replacement knee prosthesis assembly of claim 2, wherein the cupule is formed of a plastic material.

7. The replacement knee prosthesis assembly of claim 6, wherein the plastic material is polyethylene.

8. The replacement knee prosthesis assembly of claim 2, wherein the cupule comprises extended sides which extend beyond the diameter of the cavity of the cupule.

9. The replacement knee prosthesis assembly of claim 8, wherein each of the extended sides has a groove formed therein, each of the grooves is configured to permit passage of the catch, and each of the grooves is diametrically opposed with respect to the intercondylian notch.

10. The replacement knee prosthesis assembly of claim 2, wherein the cupule is immobily seated in the central cavity.

11. The replacement knee prosthesis assembly of claim 2, wherein the cupule comprises one piece and is housed within the femoral implant.

12. The replacement knee prosthesis assembly of claim 1, wherein said spherical head has a conical cavity provided therein for accommodating the end portion of the catch, and said spherical head is selected from a set of heads whose cavities have different opening angles in order to permit heads to ride higher or lower on the catch due to the different size cavities, and therefore an adjustment of the height of said spherical articulation for obtaining a proper ligamentary tension.

13. The replacement knee prosthesis assembly of claim 1, wherein said catch is offset rearwards from an axis of said intramedullary shank which corresponds to an axis of the tibial intramedullary canal, and said spherical head and catch form an integral member which is removably mounted to said tibial base.

14. The replacement knee prosthesis assembly of claim 13, wherein the catch is extended by a base plate comprising an anterior portion and slidingly mounted in a sliding member designed on the tibial base and attached to the tibial base by an appropriate fixation means.

15. The replacement knee prosthesis assembly of claim 14, wherein said fixation means is a screw passing through the base plate in its anterior portion and which can be screwed to the tibial base.

16. The replacement knee prosthesis assembly of claim 14, wherein said sliding member is formed by a pair of parallel ramps having an inverted L or dovetail shape, separated by a gap corresponding substantially to the width of a recess formed in the central area of the tibial base.

17. The replacement knee prosthesis assembly of claim 13, wherein the integral member is formed of stainless steel.

18. The replacement knee prosthesis assembly of claim 13, further comprising a set of said integral members of different heights, and a set of tibial plates of different thicknesses, whose progression corresponds to the progression of successive heights of said integral members.

19. The replacement knee prosthesis assembly of claim 18, wherein the thicknesses of the tibial bases and the heights of said integral members increase according to the same arithmetical progression.

20. A replacement knee prosthesis assembly for replacing an earlier implanted prosthesis, the replacement prosthesis comprising:

a tibial implant and a femoral implant cooperatively configured to enable a first and a second articulation between said tibial implant and said femoral implant, said femoral implant comprising a bicondylian part comprising a pair of condyles disposed so as to define an intercondylian notch and a posteriorly extending hemispherical cavity central of the pair of condyles, and said tibial implant comprising a tibial base, a catch mounted to said tibial base, and at least one disc removably mounted to said tibial base and on which said pair of condyles is rotatably slidable to provide said first articulation, said catch comprising an end portion, and a spherical head having a conical cavity for accommodating the end portion of the catch and rotatably accommodated within said central cavity of said pair of condyles so as to provide said second articulation, and said spherical head being selected from a set of heads whose cavities have different opening angles in order to permit the heads to ride higher or lower on the catch due to the different size cavities, and therefore an adjustment of the height of said spherical articulation for obtaining a proper ligamentary tension.

21. A replacement knee prosthesis kit assembly for replacing an earlier implanted prosthesis, the replacement prosthesis comprising:

a tibial implant and a femoral implant cooperatively configured to enable a first and a second articulation between said tibial implant and said femoral implant, said femoral implant comprising a bicondylian part comprising a pair of condyles disposed so as to define an intercondylian notch and a posteriorly extending hemispherical cavity central of the pair of condyles, and said tibial implant comprising a tibial base, a plurality of ball joint members mounted to said tibial base, and at least one disc removably mounted to said tibial base and on which said pair of condyles is rotatably slidable to provide said first articulation, said ball joint members being formed with a spherical head rotatably accommodated within said central cavity of said pair of condyles so as to provide said second articulation, and said ball joint member being formed in a plurality of heights and a plurality of tibial plates being formed in a plurality of thicknesses corresponding to the heights of the ball joint member in order to permit the heads to ride higher or lower on the ball joint member and therefor an adjustment of the height of said spherical head for obtaining a proper ligamentary tension.

22. A replacement knee prosthesis kit for replacing an earlier implanted prosthesis to enable a surgeon to adjust ligamentary tension, the kit comprising:

a tibial implant comprising a tibial stem adapted to be introduced into the intramedullar canal of a tibia, and a tibial base attached to the stem and comprising a slide member, a set of tibial plates formed in a progression of thicknesses, each said tibial plate having a pair of conjugated surfaces and adapted to be received on the tibial base, a femoral implant comprising a stem attached to a pair of condyles and suitably shaped to slide and be articulated upon the conjugated surfaces, said condyles forming a hemispherical cavity, and a set of ball joint members formed in a progression of heights corresponding to respective of the tibia plates, each said ball member comprising a base plate member adapted to be slidably received in said slide member, and a spherical articulation head sized to be received in said cavity, said articulation heads being adapted to ride higher or lower on the tibial plate and therefor permit an adjustment of the height of said spherical articulation head whereby a surgeon can adapt a prosthesis to each patient without having to change the tibial stem for obtaining a proper ligamentary tension.

* * * * *